US 6,692,775 B2

(12) United States Patent
Young

(10) Patent No.: US 6,692,775 B2
(45) Date of Patent: Feb. 17, 2004

(54) BACTERICIDAL GEL AND METHOD FOR TREATING BURNS AND DERMAL LESIONS

(75) Inventor: John D. Young, Seminole, FL (US)

(73) Assignee: Aqua Med, Inc., Seminole, FL (US)

(*) Notice: Subject to any disclaimer, the term of this patent is extended or adjusted under 35 U.S.C. 154(b) by 0 days.

(21) Appl. No.: 10/180,992

(22) Filed: Jun. 24, 2002

(65) Prior Publication Data

US 2002/0168387 A1 Nov. 14, 2002

Related U.S. Application Data

(63) Continuation-in-part of application No. 09/524,493, filed on Mar. 13, 2000, now Pat. No. 6,416,790.

(51) Int. Cl.$^7$ .............................. A61K 9/00; A61K 9/08; A61K 9/10; A61K 9/107; A61K 9/127; A61K 33/06; A61K 33/08; A61K 33/12; A61K 33/14

(52) U.S. Cl. .................. 424/681; 424/400; 424/405; 424/450; 424/600; 424/682; 424/683; 424/684; 424/685; 424/686; 424/687; 424/688; 424/689; 424/690; 424/691; 424/692; 424/693; 424/694; 424/695; 424/696; 424/697; 424/698; 424/722; 424/DIG. 13; 514/783; 514/786; 514/858; 514/859; 514/860; 514/861; 514/862; 514/863; 514/864; 514/865; 514/886; 514/887; 514/938; 514/939; 514/944; 514/964; 514/975; 422/28

(58) Field of Search ................................. 424/681, 400, 424/405, 450, 600, 682, 683, 684, 685, 686, 687, 688, 689, 690, 691, 692, 693, 694, 695, 696, 697, 698, 722, DIG. 13; 514/783, 786, 858, 859, 860, 861, 862, 863, 864, 865, 886, 887, 938, 939, 964, 975, 944; 422/28

(56) References Cited

U.S. PATENT DOCUMENTS

| 3,893,943 A | 7/1975 | Willard, Sr. |
| 4,029,770 A | 6/1977 | Willard, Sr. |
| 2001/0043954 A1 * | 11/2001 | Sweet .................. 424/725 |

* cited by examiner

*Primary Examiner*—John Pak
(74) *Attorney, Agent, or Firm*—Larson & Larson, PA; James E. Larson

(57) ABSTRACT

A gel formulation is combined with a bactericidal concentrate which is a liquid mixture of about 1000 parts by volume of ultra pure water having an electrical resistance of 16–26 megohms, total dissolved solids of less than 0.04 parts per million and a specific conductance of less than 0.10 mho with about 1.2 to 3 parts by volume of Willard Water as prepared in accordance with U.S. Pat. No. 3,893,943. The bactericidal liquid concentrate in the amount of 3.5 to 12 ml in one liter of gel formulation is applied directly to a skin surface area having a burn or other dermal lesion to protect the area from bacterial contamination.

6 Claims, No Drawings

BACTERICIDAL GEL AND METHOD FOR TREATING BURNS AND DERMAL LESIONS

PRIOR APPLICATION

This application is a continuation-in-part from application Ser. No. 09/524,493, filed Mar. 13, 2000, which is now U.S. Pat. No. 6,416,790.

FIELD OF THE INVENTION

This invention relates to a catalyst called Willard Water. More particularly, it refers to a bactericidal gel formed from a concentrate of the catalyst and ultra pure water mixed with a gel composition or formulation and the use of the resulting bactericidal gel concentrate to treat burns and dermal lesions.

BACKGROUND OF THE INVENTION

Willard Water is set forth in U.S. Pat. No. 3,893,943 as a novel catalyst and its preparation is therein described. Willard Water has a poor shelf life insofar as its use in a bactericidal solution. A concentrate is needed that will provide an extended shelf life and will be useful to treat epidermal body surfaces that may be contaminated with bacteria.

The concentrate needs to be kept moist under a wound dressing such as a polymeric or hydrocalloid membrane. Such dressings are expensive. A formulation is needed that can be employed for use with a dry dressing such as inexpensive cotton gauze.

SUMMARY OF THE INVENTION

The present invention solves the above problem by providing a bactericidal gel made from the concentrate. The concentrate is made with a liquid mixture ratio of about 1.2 to 3 ml of Willard Water to about one liter of ultra pure water having an electrical resistance of 16–26 megohms, total dissolved solids of less than 0.04 parts per million and a specific conductance of less than 0.10 mho. The Willard Water employed in the concentrate is as described in U.S. Pat. No. 3,893,943. The concentrate in a gel formulation is used to apply to the epidermis of patients to control bacterial contaminations. A gel for treatment of burns, psorriais and abrasions is formed from one liter of a gel formulation containing about 3.5–12 ml of the concentrate at a pH of 7.5 to 9.7. The concentrate of this invention has a shelf life in a plastic container of at least two and one half years compared to a shelf life of Willard Water combined with distilled water of less than seven months.

DETAILED DESCRIPTION OF THE INVENTION

The liquid bactericidal concentrate of this invention is made from 1.2 to 3 parts by volume of Willard Water made according to the description of the catalyst described in U.S. Pat. No. 3,893,943, incorporated herein by reference, to 1000 parts by volume of ultra pure water.

The ultra pure water is made by first passing potable water through a 5 micron sediment filter and then through a granulated activated charcoal bed having a depth of about 20 cm. The water is then passed through a 1.2 cubic foot mixed bed deionizer resin such as SIBRON Model No. NM-60. The resulting treated water is passed twice through a standard reverse osmosis process utilizing Model FC-018A filters obtained from Water Link Technologies, Inc. and then through a 0.2 micron filter to obtain ultra pure water having an electrical resistance of 16–26 megohms, total dissolved solids of less than 0.04 parts per million and a specific conductance of less than 0.10 mho.

The ultra pure water is mixed in a holding drum with the Willard Water at varying ratios of 1000 to 1.2–3 parts by volume depending upon the bacteria for which control is sought.

About 1.2 ml of Willard Water is added to one liter of the ultra pure water to create a liquid mixture for treatment of Staphylococcus. Streptococcus, *E. coli* and Pseudomonas bacteria. In treating burns with a liquid, 2.8 ml of Willard Water is added to one liter of the ultra pure water. The solutions are buffered to a pH of 8.0 to 8.5.

For further treatment of burn victims, a gel is formed containing 3.5 to 12 ml of the liquid concentrate in 1000 ml of a gel formulation. The gel formulation will contain sodium silicate, sulfate of ester of oil of Euphorbiaceae, magnesium and calcium chloride, glycerin, xanthan gum, methanol, paraben, potassium sorbate and sodium benzoate. The gel formulation should be buffered to a pH of 7.5 to 9.7. Another gel formulation contains 3.5 to 12 ml of the liquid bactericidal concentrate in one liter of a 2% methylcellulose composition. The one liter will contain 20 grams of methylcellulose, 2 grams of sodium benzoate and the remainder purified water.

The gel concentrate is applied directly to a patient's skin surface containing a burn or other lesion. The burn or lesion begins healing within a few days without being affected by bacterial contamination. A cotton gauze is placed over the gel concentrate to protect the wound.

COMPARATIVE EXAMPLES

A double blind study was carried out to compare the shelf life of Willard Water concentrate in 1000 ml distilled water (concentrate A) with a Willard Water concentrate containing 1.2 ml of Willard Water to 1000 ml of ultra pure water (concentrate B). A quantity of each of the concentrates had been stored for three years in 8 oz. plastic bottles.

Concentrate A

The liquid formulation contained in the 8 oz. bottle was applied to a filter paper which was smeared with *Staphylococcus aureus* in a neutral agar and tested in accordance with a 0.5 McFarland standard. No effect was noted in the *Staphylococcus aureus* growing on the filter paper.

Concentrate B

The liquid formulation contained in the 8 oz. bottle was applied to a filter paper which was smeared with *Staphylococcus aureus* in a neutral agar and tested in accordance with a 0.5 McFarland standard. The *Staphylococcus aureus* did not grow on the filter paper and was sensitive to the formulation on the filter paper.

The above description has described specific formulations prepared according to the teachings of this invention. The inventive concept is not limited to the higher range of Willard Water to ultra pure water but includes equivalents that can be formulated without causing injury to the patient.

Having thus described the invention what is claimed and desired to be secured by Letters Patent is:

1. A bactericidal concentrate in a gel formulation comprising:

(a) a liquid mixture ratio of about 1000 parts by volume ultra pure water having an electrical resistance of 16–26 megohms, total dissolved solids of less than 0.04 parts per million and a specific conductance of less than 0.10 mho;

(b) mixed with 1.2 to 3 parts by volume of catalyst micelles to provide a bactericidal concentrate, wherein said catalyst micelles are prepared by admixing a water soluble alkali metal silicate with an aqueous medium containing a dissolved substance which is a source of calcium ion and a dissolved substance which is a source of magnesium ion;

the aqueous medium containing the dissolved substances in amounts to provide between about $1\times10^{-4}$ and $1\times10^{-1}$ mole per liter each of calcium ion and magnesium ion;

the aqueous medium containing the dissolved substances in amounts to provide a molar ratio of calcium ion to magnesium ion between about 2.0:1.0 and 1.0:2.0;

reacting the alkali metal silicate with the dissolved substances providing calcium ion and magnesium ion to produce an aqueous suspension of finely divided particles of the reaction product;

admixing a micelle-forming surfactant with the aqueous medium in an amount to form catalyst micelles comprising the finely divided particles of the reaction product upon agitating the aqueous medium; and agitating the aqueous medium containing the finely divided particles of the reaction product and surfactant to form the catalyst micelles; and (c) one liter of a gel formulation in combination with 3.5–12 ml of the bactericidal concentrate from (a) and (b).

2. The bactericidal concentrate in a gel formulation according to claim 1 wherein the one liter gel formulation further contains a 2% by volume methylcellulose composition.

3. The bactericidal concentrate in a gel formulation according to claim 2 wherein in the gel formulation there are 20 grams of methylcellulose, 2 grams of sodium benzoate and a remainder purified water to volume of one liter.

4. The bactericidal concentrate in a gel formulation according to claim 1, wherein the one liter gel formulation contains sodium silicate, sulfate of ester of oil of Euphorbiaceae, magnesium and calcium chloride, glycerin, xanthan gum, methanol, paraben, potassium sorbate and sodium benzoate buffered to a pH of 8 to 8.5.

5. Method of treating a burned area on a patient's skin comprising applying a bactericidal concentrate in a gel formulation according to claim 1 to the burned area.

6. The method according to claim 5 wherein a cotton gauze is applied over the bactericidal concentrate in a gel formulation.

* * * * *